United States Patent [19]

Codner

[11] Patent Number: 5,686,304
[45] Date of Patent: Nov. 11, 1997

[54] CELL CULTURE APPARATUS AND METHOD

[75] Inventor: Meryl Codner, St. Paul, Minn.

[73] Assignee: Avecor Cardiovascular, Inc., Plymouth, Minn.

[21] Appl. No.: 574,452

[22] Filed: Dec. 15, 1995

[51] Int. Cl.$^6$ .......................... C12N 5/00; C12N 5/02
[52] U.S. Cl. .................... 435/325; 435/383; 435/283.1
[58] Field of Search ........................ 435/240.1, 283.1, 435/240.25, 325, 383; 210/500.21; 428/411.1, 429, 447

[56] References Cited

U.S. PATENT DOCUMENTS

| | | | |
|---|---|---|---|
| 3,102,082 | 8/1963 | Brewer | 435/30 |
| 3,489,647 | 1/1970 | Kolobow | 435/2 |
| 3,510,387 | 5/1970 | Robb | 428/220 |
| 3,941,662 | 3/1976 | Munder et al. | 435/286.1 |
| 3,969,240 | 7/1976 | Kolobow | 210/646 |
| 4,093,515 | 6/1978 | Kolobow | 435/2 |
| 4,140,162 | 2/1979 | Gajewski et al. | 435/297.5 |
| 4,142,940 | 3/1979 | Modelell et al. | 435/297.1 |
| 4,661,455 | 4/1987 | Hubbard | 435/240.241 |
| 4,829,002 | 5/1989 | Pattilo et al. | 435/297.1 |
| 4,847,462 | 7/1989 | Soodak | 219/121.63 |
| 4,937,194 | 6/1990 | Pattilo et al. | 435/240.2 |
| 4,945,203 | 7/1990 | Soodak | 219/121.64 |
| 5,008,197 | 4/1991 | Wergeland | 435/240.24 |
| 5,149,649 | 9/1992 | Miyamori et al. | 435/240.242 |
| 5,225,346 | 7/1993 | Matsumiya et al. | 435/284 |
| 5,288,631 | 2/1994 | Baumgartner et al. | 435/240.242 |
| 5,350,080 | 9/1994 | Brown | 220/465 |
| 5,362,642 | 11/1994 | Kern | 435/240.1 |

FOREIGN PATENT DOCUMENTS

| | | | |
|---|---|---|---|
| 214178 | 9/1988 | Japan | |
| 2255571 | 11/1992 | United Kingdom | 435/284.1 |
| 2268187 | 6/1994 | United Kingdom | 435/284.1 |

OTHER PUBLICATIONS

R.I. Freshney, Chapter 1, "Introduction to basic principles", in *Animal Cell Culture: A Practical Approach*, 2d Ed., IRL Press (1994).

B. Griffiths, "Scaling-up of animal cell cultures", Chapter 3 in *Animal Cell Culture: A Practical Approach*, 2d Ed., IRL Press (1994).

"Bubble-Free Oxygenation by Means of Hydrophobic Porous Membranes", *Enz. Microb. Tech.*, 17(9):839 (1995)).

Lemoli et al. Experimental Hematol. 1992. vol. 20, pp. 569–575.

*Primary Examiner*—Blaine Lankford
*Assistant Examiner*—Christopher R. Tate
*Attorney, Agent, or Firm*—Fredrikson & Byron, P.A.

[57] ABSTRACT

A cell culture apparatus formed of a plurality of thin (e.g., 0.005" or less), spaced, gas-permeable, silicone membranes sealed at their edges to form a bag-like vessel comprising one or more interior chambers suitable for containing cell culture media. A suitable portion of the membrane surfaces are of suitable thickness and surface area to provide structural integrity to the apparatus and sufficient gas permeability for cell growth within the chamber.

24 Claims, 5 Drawing Sheets

CELL CULTURE APPARATUS AND METHOD

TECHNICAL FIELD

The present invention relates to cell culture apparatuses and methods, and particularly to cell culture apparatuses in the form of cell culture bags and similar devices. In another aspect the invention relates to silicone membranes, such as those used to prepare oxygenators for biological fluids.

BACKGROUND OF THE INVENTION

The culture of mammalian cells and tissues is now quite common in the areas of molecular biology and biotechnology. Several textbooks provide guidance in the materials and methods involved in preparation, sterilization, and cell propagation. See, for instance, R. I. Freshney, Chapter 1, "Introduction to basic principles", in *Animal Cell Culture: A Practical Approach*, 2d Ed., IRL Press (1994).

A variety of cell types can now be grown in culture, including connective tissue cells, skeletal, cardiac, and epithelial cells, neural cells, endocrine cells, melanocytes, and many types of tumor cells. Similarly a variety of media are available, depending on the particular growth requirements of the cells and the growth conditions.

Depending on the type of cells, their intended use, and the conditions of growth, cells can be grown in a number of different configurations. Most cultures are propagated in the form of a monolayer, with the cells anchored to a glass or plastic substrate. Some, however, are preferably grown in suspension, which has the advantage of simpler propagation. Using suspension, subculture can be accomplished by simple dilution rather than by detaching (e.g., by trypsinization) the cells from anchored growth. Growth in suspension also provides increased surface area with increased bulk, as well as improved ease of harvesting, and the possibility of achieving a "steady state" culture.

Growth in suspension is hampered, however, by a number of factors that do not affect monolayer cultures. See, for instance, B. Griffiths, "Scaling-up of animal cell cultures", Chapter 3 in *Animal Cell Culture: A Practical Approach*, 2d Ed., IRL Press (1994), the disclosure of which is incorporated by reference.

Cell growth kinetics in suspension culture can be affected by a number of considerations. The effect of varying growth conditions can be important, such as the growth temperature, initial growth phase of cells, inoculation density, stirring rate, and medium surface area. So, too, can the selection of medium, nutrients, and pH all affect growth in a predictable, controllable manner.

The scale-up of animal cell cultures is particularly dependent on the ability to supply sufficient oxygen without causing cellular damage. Since oxygen is typically only sparingly soluble in culture media, it is often necessary to supply oxygen to the medium throughout the life of the culture. Typically, a culture can be aerated by one, or a combination, of the following methods: surface aeration, sparging, membrane diffusion, medium diffusion, increasing the partial pressure of oxygen, and/or increasing the atmospheric pressure. M. Schneider, et al., for instance, recently described the application of bubble-free aeration to animal cell culture processes to avoid shear stress and foaming often associated with direct sparging. (See "Bubble-Free Oxygenation by Means of Hydrophobic Porous Membranes", *Enz. Microb. Tech.*, 17(9):839 (1995)).

Typically, cell culture production of either cells or cell-secreted products begins with the small scale growth of cells. Traditional vessels for small volume cultures include multi-well plates, T-flasks, roller bottles and spinner flasks. Most small-scale cultures are limited to 5 to 7 days of growth. Final cell densities and total cell numbers are frequently low due to space, surface area and gas exchange limitations. Thus, it is frequently necessary to use multiple vessels to grow a desired cell population. The use of multiple vessels, however, means increased labor and contamination risk due to the need to open, close, fill and harvest from each vessel.

In recent years a number of manufacturers have also begun to offer cell culture devices in the form of flexible, disposable bags formed of biologically inert and gas-permeable plastic materials such as fluoroethylenepropylene copolymers. U.S. Pat. Nos. 4,847,462 and 4,945,203 (Soodak), for instance, both relate to methods and apparatuses for manufacturing air and water tight bags of plastic films, the bags being useful for culturing living cells. Cell culture bags said to be covered by these patents are available from American Fluoroseal Corporation (Columbia, Md.).

Still other patents describe the use of flexible bags as components of cell culture media systems. See, for instance, U.S. Pat. Nos. 4,937,194 and 4,829,002 (Pattilo, et al.); 5,350,080 (Brown); and 5,362,642 (Kern). Yet other patents relate to cell culture devices that involve the use of oxygen-permeable materials. GB Pat. No. 2268187 (Armstrong, et at.), for instance, describes a vessel having part of its walls formed as a gas-permeable membrane. The vessel may be a petri-dish whose base consists of the membrane, such as silicone rubber. Alternatively, it may be a Roux bottle in which a side wall comprises the gas-permeable membrane.

GB Pat. No. 2255571 (Burr, et al.) describes a method of cell culture involving placing cells in a culture medium on a silicone membrane and periodically feeding the cells, and JP 2234670 describes the use of a shell membrane as the earlier for culturing an adhesive animal cell.

Similarly, U.S. Pat. No. 4,661,455 (Hubbard) relates to a double membrane bag assembly for supplying nutrients and oxygen to growing cells. The device relies on the use of gas permeable membranes such as those formed of dimethyl silicone. U.S. Pat. No. 5,008,197 (Wergeland) describes an apparatus for cultivating cells that involves the use of an oxygen-permeable membrane (such as a "silicone membrane") to supply oxygen to the media. Finally, U.S. Pat. No. 5,288,631 (Baumgartner, et al.) describes a tubular membrane for the delivery of gaseous fluid to a surrounding medium, for use in oxygenating an animal cell reactor.

On a separate subject, gas-permeable silicone rubber membranes have themselves been described as useful for a number of products, such as blood oxygenators. The preparation and use of such silicone rubber membranes is described, for instance, in U.S. Pat. Nos. 3,489,647 (Kolobow I), 3,969,240 (Kolobow II) and 4,093,515 (Kolobow III and 3,510,387 (Robb). Such membranes can be provided either with an integral support material (e.g., with a fabric scrim) or in unsupported form. They can also be provided in a form where one or more of the silicone layers is compounded with a filler, such as fumed silica or carbon black.

As far as Applicant is aware, silicone rubber membranes have not previously been suggested or used for the purpose of fabricating cell culture devices in the form of bags or envelopes. Yet, what is clearly needed are new and improved means for culturing cells, particularly those that facilitate improved oxygen supply.

SUMMARY OF THE INVENTION

The present invention provides a cell culture apparatus comprising a cell culture bag having thin, gas-permeable silicone rubber membrane walls. Preferably, the membrane is formed as a reinforced laminate of silica-filled rubber silicone layers, the laminate having a thickness on the order of 0.005 inches (0.127 mm) or less. An apparatus of the invention can provide gas exchange rates that are one or more orders of magnitude higher than most conventional cell culture bags. The higher gas exchange rate results in significantly higher cell densities and well viabilities.

In a preferred embodiment, the apparatus comprises a plurality of thin, gas-permeable, silicone rubber membranes sealed at their edges to form a waterproof bag-like vessel comprising one or more interior chambers suitable for containing cell culture media. The membranes are of suitable thickness and surface area to provide structural integrity to the apparatus and sufficient gas permeability to accommodate cell growth within the chamber.

The apparatus provides a surprising and optimal combination of such properties as gas (including $O_2$ and $CO_2$) permeability, structural integrity, optical transparency and clarity, temperature resistance, vapor transmission, resilience, temperature tolerance, low extractables, adaptability, and cost. The apparatus provides optimal spatial efficiency for use in propagating suspension cultures and microcarrier-attached cultures. The apparatus can be GMP manufactured, and is capable of being sterilized at the time of manufacture or at any time prior to use.

In a particularly preferred embodiment, the thickness of one or more membranes making up the vessel is on the order of 0.003" (0.076 mm) or less, and the apparatus further comprises a plurality of inlet/outlet ports flowably connected to one or more interior chambers of the vessel.

In another aspect, the present invention provides a method of preparing a cell culture apparatus as presently described. In yet another aspect, the invention provides a combination comprising a vessel of the present invention in combination with cell growth medium, as well as a combination of a vessel, medium, and cells. In a related aspect, the invention provides a method of culturing cells that involves the use of a cell culture apparatus as described herein.

DETAILED DESCRIPTION

Figure 1:
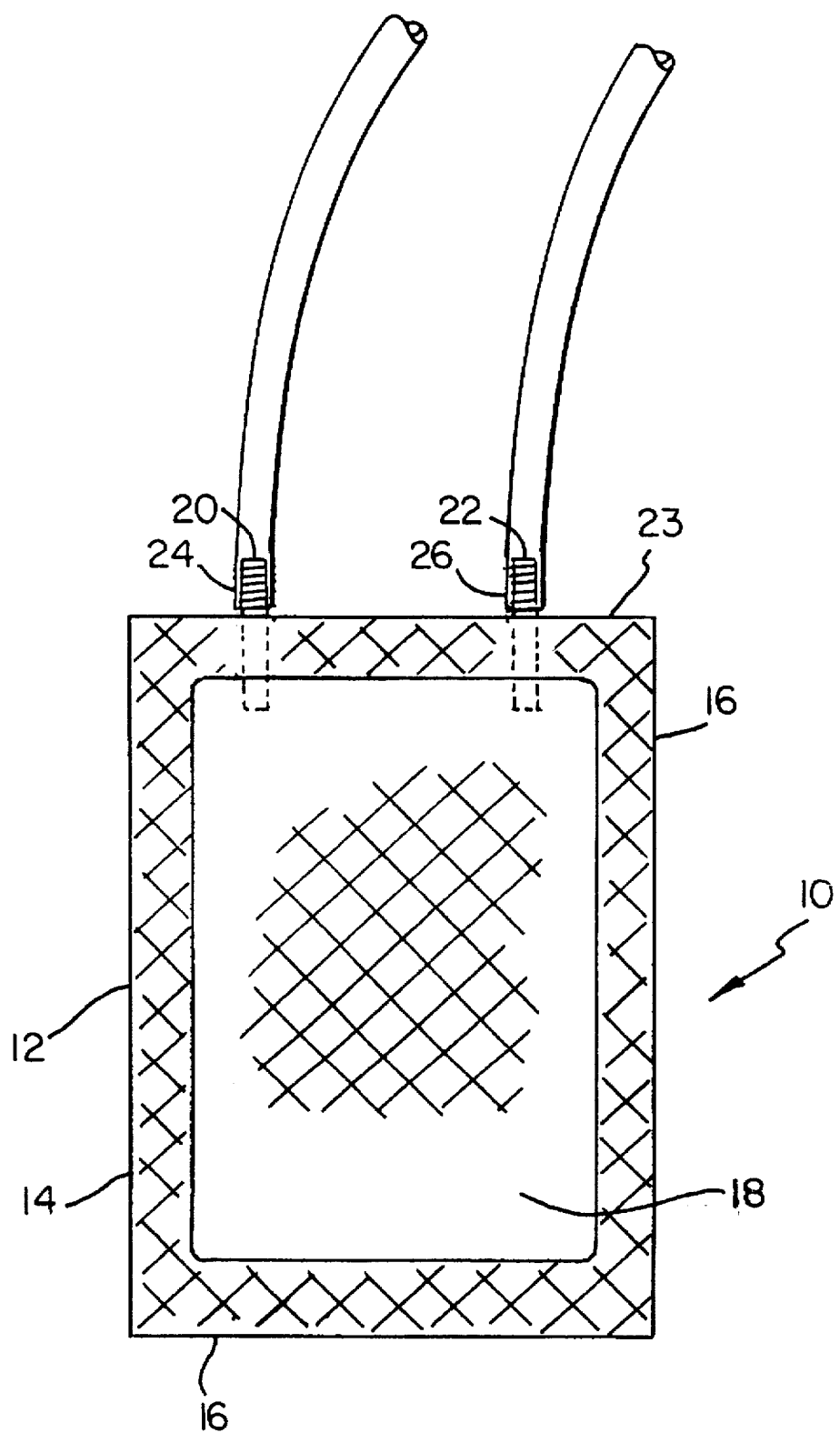
FIG. 1 shows a perspective view of a cell culture apparatus in accordance with the invention.
Figure 2:
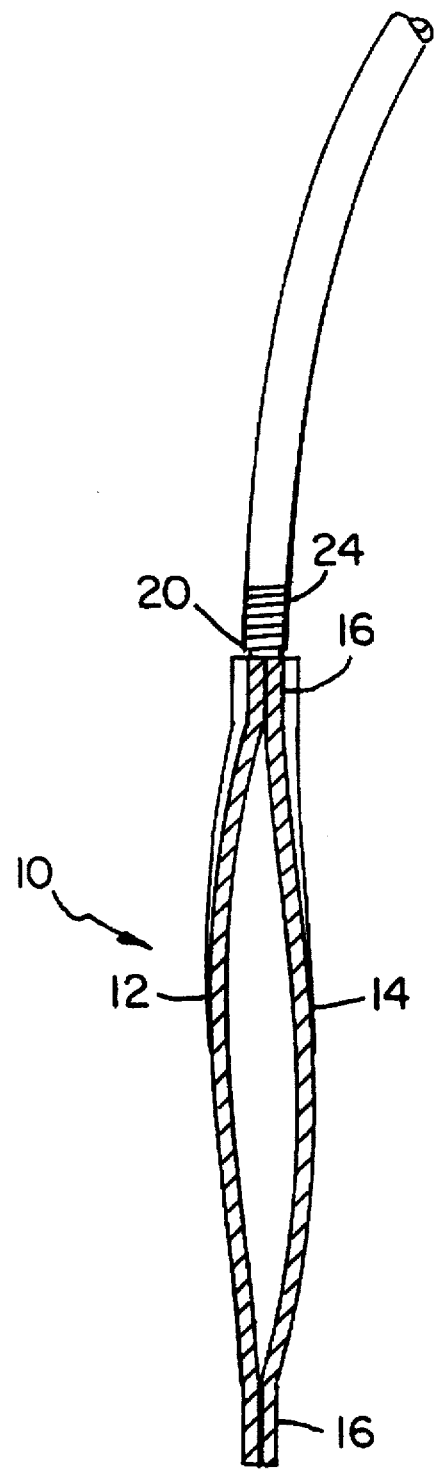
FIG. 2 shows a cross-sectional view of the apparatus shown in FIG. 1.

A preferred apparatus of the invention will be described with reference to the Drawing. In FIGS. 1 and 2 there is shown an apparatus 10, formed of two opposing silicone membranes, designated 12 and 14, respectively. The membranes are sealed together at their edges 16 to form a water-tight seal, and in turn, creating interior chamber 18.

Shown also are inlet and outlet ports 20 and 22, respectively, which provide for the flow of fluids (and/or gasses) through the top portion 23 of the apparatus and into chamber 18. The inlet/outlet ports can be used for any suitable purpose, such as the delivery of media, cells, and/or gasses. They can also be used for removal of media, cells, waste or reaction products, and the venting or withdrawal of vapors or gasses. As shown in FIG. 1, ports 20 and 22 are each preferably provided with spring-like barbs, in the form of internal coiled wires 24 and 26, respectively, in order to provide additional support and flexibility in the course of repeated and prolonged use.

An apparatus of the invention can be prepared using materials and techniques within the skill of those in the respective art, given the present teaching. Preferably, the materials used to fabricate components of an apparatus are themselves inert and biocompatible (e.g., USP XXII Class VI biocompatible).

Silicone membranes for use in this invention can be obtained or prepared using conventional techniques for the preparation of gas-permeable membranes. Cross-linked silicone polymers of appropriate molecular weight provide elastomeric properties, and can be used to prepare either RTV rubbers or heat-cured rubbers. Suitable membranes can be obtained from a number of sources, and can be prepared by conventional techniques. See, for instance, "Silicones", pgs. 1048–1059 in *Concise Encyclopedia of Polymer Science and Engineering*, Kroschwitz, J. ed., Wiley & Sons, 1990.

Preferred membranes comprise an organosilicone rubber of the type described in U.S. Pat. Nos. 3,489,647 (Kolobow I), 3,969,240 (Kolobow II) and 4,093,515 (Kolobow III) and 3,510,387 (Robb), as well as in Robb, "Thin Silicone Membranes—Their Permeation Properties and Some Applications", *Ann. NY Acad. Sci.*, 146:119–137 (1968), the disclosures of each of which are incorporated herein by reference. Particularly preferred membranes are provided as a reinforced laminate of a plurality of silicone rubber layers, one or more of the layers being compounded with a filler (e.g., fumed silica).

Suitable reinforcing means are described, for instance, at col. 5, line 62 to 6, line 13 of the '515 patent. Suitable filler materials are selected from the group consisting of filler-free silicone rubber, silicone rubber compounded with silica filler, and silicone rubber compounded with carbon black filler are preferred. For routine cell culture applications, most preferred are those prepared using silica filler. Preferred rubber materials employ a filler in mounts up to about 30%, preferably up to about 40%, and more preferably up to about 50% by weight, based on the dried weight of the membrane.

Conventional silicone membranes are prepared using a conventional process involving the formation of a toluene dispersion and peroxide cure. Alternatively, membranes can be prepared using a more recently developed processes such as those involving a solventless liquid silicone starting material and a platinum cure. Platinum-cured membranes are preferred in a number of respects, since they will typically tend to be free of residual toluene and decomposition products that may be present in peroxide cured products. Peroxide-cured products are preferred, however, for their ability to resist the formation of pinholes or other imperfections in the course of extended handling and use.

Silicone membranes used to fabricate vessels of the present invention are preferably thin, in order to improve their gas transfer and other desirable properties. Surprisingly, membranes having a thickness of on the order of 0.005" (0.127 mm) or less provide an optimal combination of such properties as gas transfer and structural integrity for use in the present invention. Particularly preferred are those having a thickness of on the order of 0.003" (0.076 mm) or less.

Figure 3:
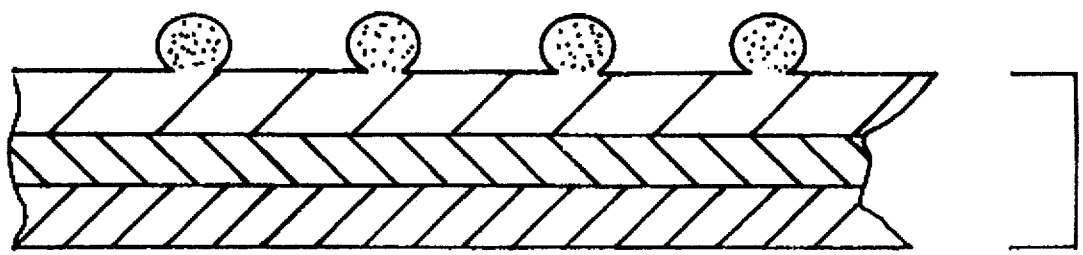
FIG. 3 shows a magnified cross-sectional view of a membrane used to form the apparatus of FIG. 1.

The thickness of a membrane can be determined using conventional methods, e.g., by gravimetric or visual means. Preferably, the thickness of a membrane is determined by microscopic evaluation in the following manner. A membrane is placed on a clean microscope slide and cut with a sharp blade to the size and shape of the slide using the slide as a template. A second clean glass slide is applied to the opposite surface of the membrane, and the resulting sandwich is retained in the jaws of a small clamp or vice as a dye material is applied to the exposed edge of the membrane. The thickness of the membrane is visually determined using standard techniques, by comparison to the gradations within a calibrated "Filar" eyepiece when used with a suitable optical microscope (e.g., a Leeds microscope). With a reinforced membrane, the thickness is, determined as the thickness of the silicone laminate itself, as opposed to the periodic extensions formed by the reinforcing fabric. (See, e.g., the cross-sectional view of FIG. 3).

In the course of fabricating an apparatus of the present invention, silicone rubber membrane materials can typically be provided in bulk form, e.g., in rolls. Pieces of suitable size are cut and paired together to form a bag of desired dimensions. Ports and/or tubes can be placed in desired positions between the paired membranes, and the bags glued or welded shut by the formation of seams at their edges. In order to achieve optimal support, reinforced membranes are preferably positioned such that their nonreinforced surfaces face each other, and in turn, with their reinforced surfaces in an outward orientation.

Bags are preferably sealed by a method that provides a durable, waterproof seal yet retains the structural integrity of the bag. Examples of suitable sealing means include the use of a suitable adhesive (e.g., an room temperature vulcanizing "RTV") silicone glue), interspersed and cured between the opposing membrane surfaces. Examples of suitable adhesives are described, for instance, in Skeist (ed.), *Handbook of Adhesives*, 3rd Ed., Chapt. 30, "Silicone Adhesive Sealants and Adhesives", J. W. Dean, (1990). Alternative sealing means include the use of a clamping mechanism to hold two opposing membranes together. Another alternative provides that an integral membrane that is itself molded or formed into the shape of a bag-like vessel. Yet another alternative provides two opposing membrane surfaces that are configured to be sufficiently matable, as in the manner of a "zip-lock" like pressure fit seal.

Preferably, the membranes are sealed by the use of a medical grade, RTV silicone glue. For example, using two pieces of silicone rubber membrane, a bead (approx. 1/16) of suitable glue was applied from a syringe to one surface (the non-reinforced surface) of one membrane, approximately 0.5 inches from the edge. A tube assembly was positioned along a short side of the membrane, and extra glue was applied around the tube assembly. The second, opposing membrane was applied over the glue and the glue was tapered until it became flattened (without working over the edge of the membrane). With a sheet of wax paper placed over the assembly, the apparatus was flattened (and worked around the tube assembly) with a roller, keeping the glue seam as straight as possible. The glue was allowed to fully cure, and the bag was used as a receptacle for media.

The component pieces, and/or bags themselves, can be cut to the desired dimensions either prior to or following the sealing process. Bags can be prepared, for instance, having any desired combination of dimensions, nominal maximum capacity, and total surface area. The nominal capacity of suitable culture bags will typically range between about 20 ml and about 1000 ml. Volumes less than about 20 ml tend to be more conveniently used in other culture formats, while volumes over about 1000 ml tend to exceed the strength limits of even reinforced silicone membranes.

Those skilled in the art will appreciate the selection of suitable port and attachable tubing materials available for such purposes. Preferably, the port and tubing materials are flexible, inert, pliable, durable, and capable of being sterilized using conventional techniques (e.g., autoclaving, ethylene oxide, gamma irradiation).

The inlet/outlet port can be provided in any convenient and suitable configuration, and tubing can be attached to the bag by a number of means. Typically, a single apparatus will provide one or more inlet ports for each compartment within the vessel. Each port can be fitted with quick connect couplers and attachment sites, either at the surface of the membrane or separated from it by a distance of flexible tubing extending outwardly from the edge. For instance, a short distance of tubing can be fitted on its distal end with a female luer lock and cap in order to facilitate its attachment to other tubing or devices. Ports and tubing are preferably of standard types and dimensions, e.g., to facilitate tubing sets having 3/8 inch inner diameter.

The bulk silicone membrane materials, and the apparatus fabricated from such materials, should be handled carefully in order to avoid the formation of pinholes, bubbles, cracks, delaminations and other structural or visible flaws or imperfections. An apparatus of the invention can be provided individually packaged in non-sterile but autoclavable pouches which can be sterilized by the user, for instance, at 121° C., at 1 atm for 20 minutes prior to use. Unsterilized pouches, in turn, are stable upon storage at ambient conditions.

An apparatus of the invention can be used to culture cells using materials, methods and techniques within the skill of those in the art. Typically, the apparatus will be sterilized and aseptically attached via its inlet port to a sterilized tubing assembly that, in turn, is aseptically attached to a sterile media filter. The filter, in turn, is attached to a sterile or non-sterile media reservoir. Closing the clamp on the outlet port of the apparatus, the reservoir is used to fill the apparatus to the desired level. When filled, the inlet port is closed or clamped shut, and both ports can be wiped with alcohol and covered.

The invention will be further described with reference to the following non-limiting Examples.

EXAMPLES

EXAMPLE 1

Cell Growth Comparisons

The following three commercially available polymeric bags were each compared with an apparatus of the present invention for use in cell growth using a standard hybridoma cell culture: Teflon bags (American Fluoroseal), polyolefin bags (Fenwal), and ethylene vinyl acetate copolymer ("EVA") bags (Stedim Co.). Due to differences in size or recommended volume, media volume and initial cell inoculum were normalized according to the surface area of the various bags. Bags were initially fried with 0.4 ml/cm$^2$ of medium (Dulbecco's Minimal Essential Medium High Glucose ("DMEM HG") supplemented with 10% fetal bovine serum ("FBS") and 6 mM glutamine) for each cm$^2$ of bag surface area. On day one, 0.15×10$^6$ cells/ml were added to each bag. All bags were placed in a 37° C. incubator at 85-90% humidity and place on a rocker set to agitate at 90 sec/cycle. The incubator was maintained at 10% $CO_2$ in air. Cell samples were taken daily. Each bag was fed with additional medium in order to maintain the cells in log phase until an upper media volume of 1.6 ml/cm$^2$ was reached. Total length of the study was 163 hours.

Figure 4:
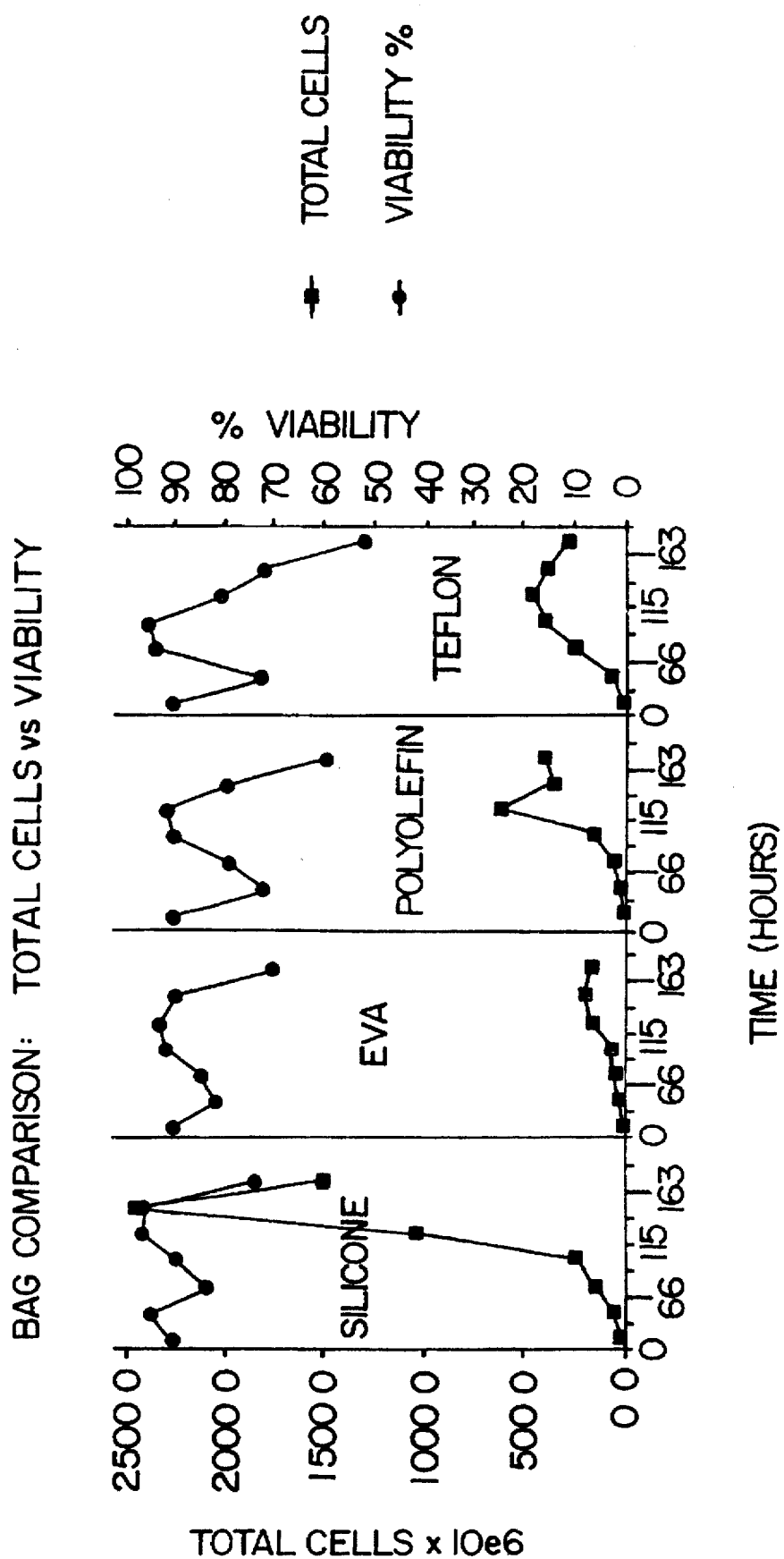
FIG. 4 shows a chart comparing total cell growth to cell viability, for culture bags fabricated from various materials.

The results of the study are shown in FIG. 4. It can be seen that the silicone bag had at peak a cell density of $3.6\times10^6$ cells/ml with viability of 98%. This is over four-fold higher than the next closest bag. Total cells produced by the silicone bag at peak was $2.5\times10^9$ at 98% viability.

EXAMPLE 2

Maximum Cell Growth Study

A study was conducted using cell culture bags of the present invention. The objective of the study was to culture conventional hybridoma cells in order to achieve maximum cell count and viability with a minimum number of growth vessels. Hybridoma cells were grown in the manner described in Example 1, although using a 600 ml culture bag of the invention. The results of the study are shown in TABLE I below:

TABLE I

| Time (hours) | Total # cells (× 10e6) | Viability (%) |
| --- | --- | --- |
| 0 | 25.95 | 92 |
| 40 | 64.01 | 96 |
| 66 | 162.62 | 85 |
| 91 | 262.96 | 91 |
| 115 | 1065.68 | 98 |
| 138 | 2491.20 | 98 |
| 163 | 1529.32 | 75 |

These results demonstrate that a 600 ml cell culture bag of the present invention provided approximately $2.5\times10^9$ cells with 98% viability at peak. Assuming the typical cell density achieved using a standard flask (e.g., of the "T-225" type) to be $0.7\times10^6$ cells/ml, it would require 36 flasks at 100 ml each to produce same number of cells. It is believed that the high gas exchange properties of the silicone bag can be attributed to the increased cell growth and viability. These results clearly show that the cell culture bag is excellent for preduction-seale inoculations.

EXAMPLE 3

Recombinant Protein Production

Recombinant protein production by mammalian cells is highly dependent on the overall cellular environment. It is known that as a cell population increases, the need for efficient control of dissolved oxygen and pH (via $CO_2$/$NaHCO_3$ buffering) is increased. Silicone membrane cell culture bags of the invention were evaluated to determine whether the higher gas exchange achievable using a bag of the present invention can provide the necessary level of $O_2$ and $CO_2$ using a standard, humidified $CO_2$ incubator.

Figure 5:
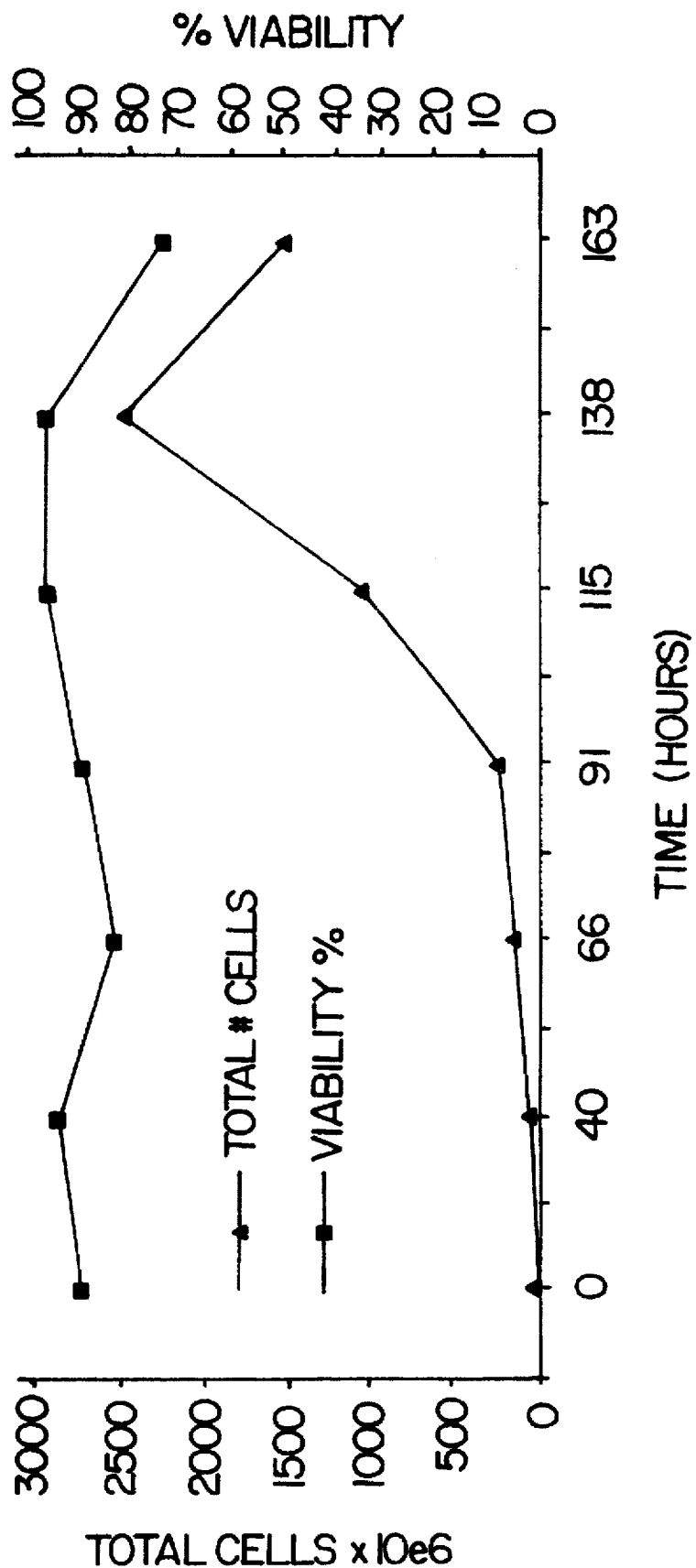
FIG. 5 shows a chart comparing total cell growth to time, for culture bags of the present invention.

A 1 liter Teflon bag, and a 1 liter bag of the present invention were each inoculated $1\times10^5$ cells/ml to final volumes of 400 ml per bag. Each bag type was cultured 10 days in a humidified $CO_2$ incubator with cell counts, viabilities, pH, glucose, lactic acid and recombinant protein measurements done daily. Results of pH and recombinant protein production in both µg/ml and µg per $10^5$ cells are shown in FIG. 5.

Results clearly show elevated recombinant protein production with the silicone membrane bag in both µg/ml and µg per $10^5$ cells. This increase in protein production is believed to be due to enhanced gas exchange across the silicone membrane. The silicone cell culture bag has gas permeability rates that are orders of magnitude higher than commercial bags formed of a Teflon-brand material. Evidence of increased $CO_2$ control in the silicone bag was seen in the pH control. The silicone bag was 0.57 pH units closer to control medium pH than the commercial bag at experiment end. The results dearly show that the silicone membrane bag was ideal for recombinant protein production by mammalian cells.

It is to be understood that the invention is not intended to be limited to the above embodiments, which are shown for purposes of illustration in the Drawing and described above, but is intended to include any modification or variation thereof falling within the scope of the appended claims.

What is claimed is:

1. An apparatus comprising a cell culture vessel comprising a thin, gas-permeable wall formed of a silicone rubber membrane, wherein the thickness of the membrane is about 0.003 inches (0.076 mm) to about 0.005 inches (0.127 mm) and the membrane is provided in the form of a reinforced laminate of filled rubber silicone layers the apparatus further comprising a plurality of inlet/outlet ports flowably connected to the vessel.

2. An apparatus according to claim 1 wherein the apparatus comprises a plurality of thin, gas-permeable, silicone rubber membranes sealed at their edges to form a waterproof vessel comprising one or more interior chambers suitable for containing cell culture media.

3. An apparatus according to claim 2 wherein the membranes are sealed together to form the vessel by the use of a medical grade silicone glue.

4. An apparatus according to claim 1 wherein one or more of the silicone rubber membranes have been compounded with silica filler at a concentration of up to about 50% by weight filler, based on the weight of the membrane.

5. An apparatus according to claim 4 wherein the silica filler is carbon black filler, at a concentration of up to about 30% by weight.

6. An apparatus according to claim 4 wherein the apparatus has a nominal capacity of between about 20 ml and about 1000 ml.

7. A method of preparing a cell culture apparatus comprising the steps of forming a thin, gas permeable silicone rubber membrane into the form of a wall of a cell culture vessel, wherein the thickness of the membrane is about 0.003 inches (0.076 mm) to about 0.005 inches (0.127 mm) and the membrane is provided in the form of a reinforced laminate of filled rubber silicone layers and providing the apparatus with a plurality of inlet/outlet ports flowably connected to the vessel.

8. A method according to claim 7 wherein the apparatus comprises a plurality of thin, gas-permeable, silicone rubber membranes sealed at their edges to form a waterproof vessel comprising one or more interior chambers suitable for containing cell culture media.

9. A method according to claim 8 wherein the membranes are sealed together to form the vessel by the use of a medical grade silicone glue.

10. A method according to claim 7 wherein one or more of the silicone rubber membranes have been compounded with silica filler at a concentration of up to about 50% by weight filler, based on the weight of the membrane.

11. A method according to claim 10 wherein the silica filler is carbon black filler, at a concentration of up to about 30% by weight.

12. A method according to claim 10 wherein the apparatus has a nominal capacity of between about 20 ml and about 1000 ml.

13. A combination comprising a cell culture apparatus comprising a cell culture vessel comprising a thin, gas-permeable wall formed of a silicone rubber membrane and a plurality of inlet/outlet ports flowably connected to the vessel, and (b) a medium for the growth of cells contained within the apparatus, wherein the combination provides a sterile environment for the introduction and growth of cells and wherein the thickness of the membrane is about 0.003 inches (0.076 mm) to about 0.005 inches (0.127 mm) and the membrane is provided in the form of a reinforced laminate of filled rubber silicone layers.

14. A combination according to claim 13 wherein the apparatus comprises a plurality of thin, gas-permeable, silicone rubber membranes sealed at their edges to form a waterproof vessel comprising one or more interior chambers suitable for containing cell culture media.

15. A combination according to claim 14 wherein the membranes are sealed together to form the vessel by the use of a medical grade silicone glue.

16. A combination according to claim 13 wherein one or more of the silicone rubber membranes have been compounded with silica filler at a concentration of up to about 50% by weight filler, based on the weight of the membrane.

17. A combination according to claim 16 wherein the silica filler is carbon black filler, at a concentration of up to about 30% by weight.

18. A combination according to claim 16 wherein the apparatus has a nominal capacity of between about 20 ml and about 1000 ml.

19. A method of culturing cells comprising the steps of
(a) providing a cell culture apparatus comprising a cell culture vessel comprising a thin, gas-permeable wall formed of a silicone rubber membrane and a plurality of inlet/outlet ports flowably connected to the vessel,
(b) adding a suitable combination of cells and medium to the chamber, and
(c) incubating the chamber under conditions suitable to propagate cell growth, wherein the thickness of the membrane is about 0.003 inches (0.076 mm) to about 0.005 inches (0.127 mm) and the membrane is provided in the form of a reinforced laminate of filled rubber silicone layers.

20. A method according to claim 19 wherein the apparatus comprises a plurality of thin, gas-permeable, silicone rubber membranes sealed at their edges to form a waterproof vessel comprising one or more interior chambers suitable for containing cell culture media.

21. A method according to claim 20 wherein the membranes are sealed together to form the vessel by the use of a medical grade silicone glue.

22. A method according to claim 19 wherein one or more of the silicone rubber membranes have been compounded with silica filler at a concentration of up to about 50% by weight filler, based on the weight of the membrane.

23. A method according to claim 22 wherein the silica filler is carbon black filler, at a concentration of up to about 30% by weight.

24. A method according to claim 22 wherein the apparatus has a nominal capacity of between about 20 ml and about 1000 ml.

* * * * *